United States Patent
Morandi et al.

(10) Patent No.: US 10,597,356 B2
(45) Date of Patent: Mar. 24, 2020

(54) PROCESS FOR THE CATALYTIC REVERSIBLE ALKENE-NITRILE INTERCONVERSION

(71) Applicant: STUDIENGESELLSCHAFT KOHLE MBH, Muelheim an der Ruhr (DE)

(72) Inventors: Bill Morandi, Muelheim an der Ruhr (DE); Xianjie Fang, Muelheim an der Ruhr (DE); Peng Yu, Muelheim an der Ruhr (DE)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 0 days.

(21) Appl. No.: 15/780,424

(22) PCT Filed: Nov. 26, 2016

(86) PCT No.: PCT/EP2016/078919
§ 371 (c)(1),
(2) Date: May 31, 2018

(87) PCT Pub. No.: WO2017/093149
PCT Pub. Date: Jun. 8, 2017

(65) Prior Publication Data
US 2019/0031602 A1 Jan. 31, 2019

(30) Foreign Application Priority Data
Dec. 1, 2015 (EP) .................. 15197353

(51) Int. Cl.
| | | |
|---|---|---|
| *C07C 253/30* | (2006.01) | |
| *B01J 31/14* | (2006.01) | |
| *B01J 31/24* | (2006.01) | |
| *C07D 209/86* | (2006.01) | |
| *C07D 209/76* | (2006.01) | |
| *B01J 27/125* | (2006.01) | |
| *B01J 31/22* | (2006.01) | |
| *B01J 31/26* | (2006.01) | |
| *C07D 209/56* | (2006.01) | |
| *C07F 7/08* | (2006.01) | |

(52) U.S. Cl.
CPC .......... *C07C 253/30* (2013.01); *B01J 27/125* (2013.01); *B01J 31/143* (2013.01); *B01J 31/2295* (2013.01); *B01J 31/24* (2013.01); *B01J 31/2404* (2013.01); *B01J 31/2409* (2013.01); *B01J 31/2457* (2013.01); *B01J 31/26* (2013.01); *C07D 209/56* (2013.01); *C07D 209/76* (2013.01); *C07D 209/86* (2013.01); *C07F 7/083* (2013.01); *B01J 2231/32* (2013.01); *B01J 2231/54* (2013.01); *B01J 2531/004* (2013.01); *B01J 2531/842* (2013.01); *B01J 2531/847* (2013.01); *C07C 2601/08* (2017.05); *C07C 2601/14* (2017.05); *C07C 2601/18* (2017.05); *C07C 2602/42* (2017.05)

(58) Field of Classification Search
CPC .................................................... C07C 253/30
See application file for complete search history.

(56) References Cited

U.S. PATENT DOCUMENTS

2011/0166376 A1    7/2011  Mastroianni

OTHER PUBLICATIONS

Fang et al.; "Catalytic reversible alkene-nitrile interconversion through controllable transfer hydrocyanation"; Science; vol. 351, Issue 6275, Feb. 19, 2016; pp. 832-836.
Kranenburg et al.; "Effect of the Bite Angle of Diphosphine Ligands on Activity and Selectivity in the Nickel-catalysed Hydrocyanation of Styrene"; J. Chem. Soc., Chem. Commun., 1995No. 21; pp. 2177-2178.
Bini et al.; "Lewis Acid Controlled Regioselectivity in Styrene Hydrocyanation"; Chem. Eur. J. 2009, vol. 15, No. 35, pp. 8768-8778.
Goertz et al.; "Application of chelating diphosphine ligands in the nickel-catalysed hydrocyanation of alk-l-enes and ω-unsaturated fatty acid esters"; Chem. Commun., 1997; vol. 16, pp. 1521-1522.
Wilting et al.; "Nickel-Catalyzed Isomerization of 2-Methyl-3-butenenitrile"; Organometallics 2005, vol. 24, No. 1, pp. 13-15.
Van Der Vlugt et al.; "Sterically Demanding Diphosphonite Ligands—Synthesis and Application in Nickel-Catalyzed Isomerization of 2-Methyl-3-Butenenitrile"; Adv. Synth. Catal., 2004, vol. 346, pp. 993-1003.
Yada et al.; "Nickel/Lewis Acid-Catalyzed Carbocyanationof Alkynes Using Acetonitrile and Substituted Acetonitriles"; Bull. Chem. Soc., Jpn., 2010, vol. 83, No. 6, pp. 619-634.

*Primary Examiner* — Joseph R Kosack
(74) *Attorney, Agent, or Firm* — Norris McLaughlin P.A.

(57) ABSTRACT

The present invention refers to processes for catalytic reversible alkene-nitrile interconversion through controllable HCN-free transfer hydrocyanation.

11 Claims, 3 Drawing Sheets

PROCESS FOR THE CATALYTIC REVERSIBLE ALKENE-NITRILE INTERCONVERSION

This application is a 371 of International Patent Application No. PCT/EP2016/078919, filed Nov. 26, 2016, which claims foreign priority benefit under 35 U.S.C. § 119 of European Patent Application No. 15197353.4, filed Dec. 1, 2015, the disclosures of which patent applications are incorporated herein by reference.

The present invention refers to processes for catalytic reversible unsaturated carbon-carbon bond-nitrile interconversion through controllable HCN-free transfer hydrocyanation wherein unsaturated carbon-carbon bond stands for a double carbon carbon bond or triple carbon carbon bond.

Organonitriles and alkenes are important synthetic intermediates with orthogonal reactivity that play a central role in the preparation of polymers, pharmaceuticals, cosmetics and agrochemicals. A process to construct or deconstruct nitrile compounds through reversible interconversion with alkenes as desired would provide an exceptionally powerful synthetic tool.

Chemical reactions that can mediate the interconversion between nonpolar functional groups and polar functional groups are of outmost importance due to the orthogonal reactivity profiles of these broad classes of chemical functional groups. The nitrile group is among the most versatile polar functionalities and is widely encountered in the preparation of polymers, pharmaceuticals, cosmetics and agrochemicals, both on industrial and laboratory scale.

Organonitriles can serve as precursors for aldehydes, acids, esters, ketones, amides, amines and heterocycles. Additionally, the electron withdrawing nature of nitriles alters the reactivity profile of a molecule and enables functionalization of neighboring positions ($\alpha$, but also $\beta$ in the case of conjugated systems).

The alkene group is a nonpolar functional group that has a distinct and complementary reactivity profile when compared to nitriles. Alkenes are tolerant to a wide range of reaction conditions commonly used to transform polar functional groups. Additionally, they can engage in a number of bond forming reactions (e.g. alkene metathesis reaction) not accessible using polar functional groups. In light of the central role played by the nitrile and alkene groups in chemical synthesis and their complementary reactivity profiles, the ability to directly interconvert nitriles with alkenes using a single catalytic protocol would likely have a broad impact across the molecular sciences.

Figure 1:
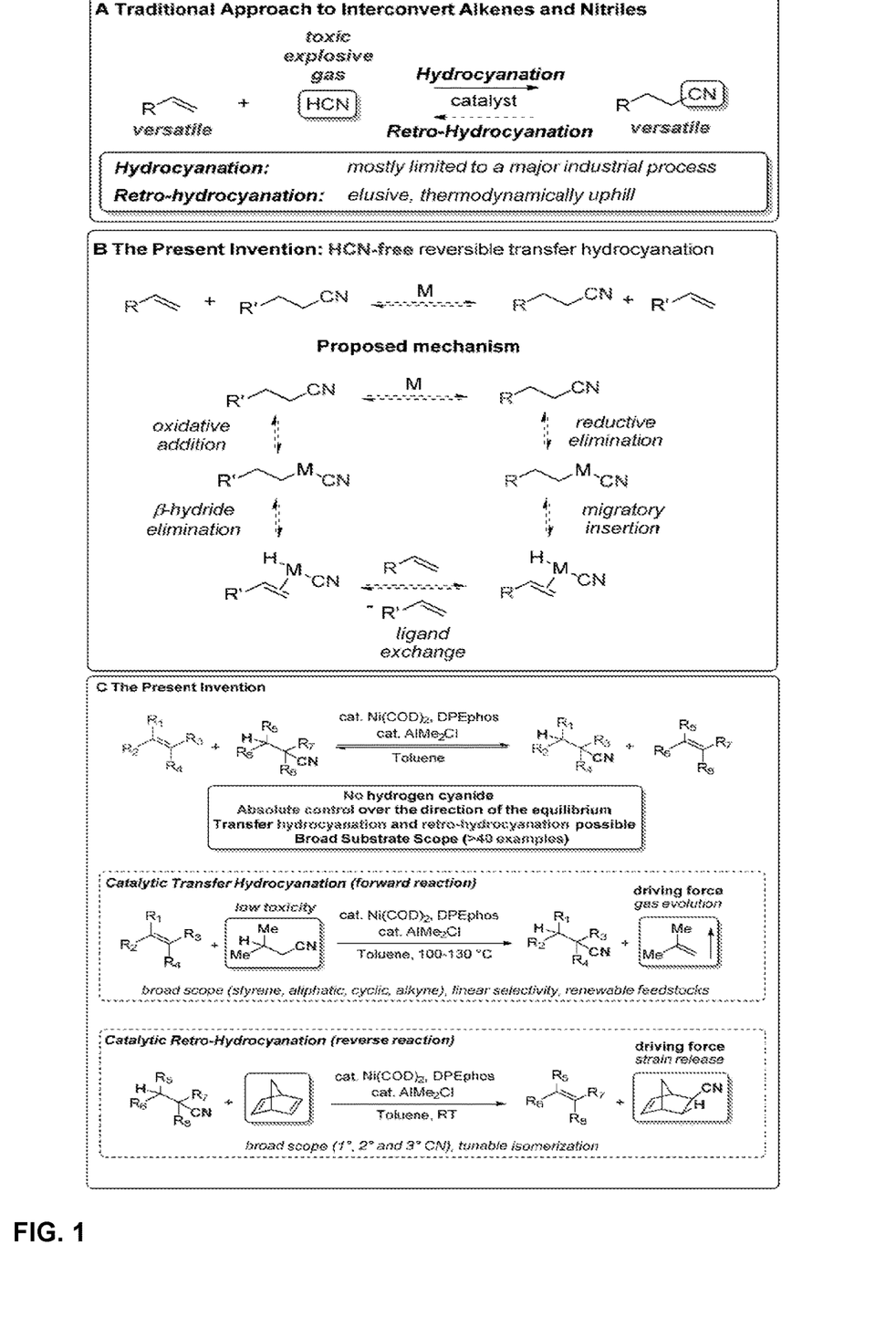
FIG. 1 shows the:
 (A) Traditional approach to hydrocyanation using HCN.
 (B) Proposed HCN-free transfer hydrocyanation reaction and mechanism.
 (C) The process of the present invention

In the prior art, the development of a broadly applicable hydrocyanation process has been hampered by the mechanistic reliance of previous approaches upon hydrogen cyanide (HCN) (FIG. 1A). HCN is an extremely toxic gas (bp 26° C.) that is both corrosive and explosive. In fact both scientists and laymen know of HCN as a chemical warfare agent and deadly poison. Although the DuPont Adiponitrile Process produces around 1 million tons/year of adiponitrile (a precursor to the polymer Nylon 6,6) through the catalytic hydrocyanation of butadiene using hydrogen cyanide (HCN) as a reagent, the alkene hydrocyanation reaction has found only very limited synthetic applications beyond the DuPont process. The lack of broad adoption of hydrocyanation is highlighted by the stark contrast to other catalytic reactions of alkenes, such as carbonylation and hydroformylation. While, theoretically, hydrocyanation could have a comparable impact to these analogous alkene transformations, the necessity to use highly toxic HCN as a reagent has greatly impeded a wider application and study of this reaction. Beyond these substantial safety concerns, the thermodynamic instability of HCN renders retro-hydrocyanation processes to produce alkenes from nitriles extremely challenging.

There is currently no catalytic and reversible group transfer reaction that permits both construction and deconstruction of a polar and versatile functional group from alkenes with absolute control over the direction of the equilibrium to selectively form, on demand, either of the functional groups.

In view of the serious hazards and limitations associated with the use of HCN, there is a need of a process for the synthesis of CN-substituted hydrocarbons without relying on the use of HCN.

Starting from the considerations of the inventors that a transfer hydrocyanation between simple alkyl nitriles and alkenes would be a powerful synthetic tool to interconvert these two synthetically versatile functional groups without relying upon HCN as a reagent, the inventors found that a metal catalyst (M) can mediate a challenging sequence of C—CN oxidative addition, β-hydride elimination, ligand exchange, migratory H-insertion and reductive elimination of C—CN bonds, and thus, a reversible transfer of H and CN can occur between alkyl nitriles and alkenes to reach a thermodynamic equilibrium (FIG. 1B). The findings of the inventors is particularly useful because:

(1) no toxic HCN is needed nor produced;
(2) both the forward reaction, hydrocyanation, and the unknown reverse reaction, retro-hydrocyanation, become accessible;
(3) either reaction pathway can possibly be favored on demand by shifting the equilibrium of the reaction using simple driving forces.

Thus, the present invention provides an HCN-free transition metal, particularly Ni-catalyzed reversible transfer hydrocyanation between alkyl nitriles and alkenes with tunable control over product selectivity (FIG. 1C).

In more detail the present invention refers to a process for the catalytic reversible alkene-nitrile interconversion wherein an unsaturated hydrocarbon (I) is reacted with an alkylnitrile (II) in the presence of a transition metal coordinated to a ligand, as a coordinated transition metal catalyst, and a Lewis acid co-catalyst, preferably in a solvent, to yield an alkylnitrile (III) and an unsaturated hydrocarbon (IV), each being different from the starting compounds, as represented in the following reaction scheme:

wherein

R$^1$, R$^2$, R$^3$ and R$^4$ can be the same or different and each independently represents H, straight chain or branched chain alkyl, cycloalkyl, heterocycloalkyl, aryl, aralkyl, heteroaryl, heteroaralkyl, each being optionally substituted by one or more groups selected from straight chain or branched chain alkyl, cycloalkyl, heterocycloalkyl, alkenyl, alkynyl, aryl, aralkyl, heteroaryl, heteroaralkyl or a heterosubstituent; or a heterosubstituent, or at least two of R$^1$, R$^2$, R$^3$ and R$^4$ may each form a cyclic 3 to 20 membered ring structure which may further be substituted by one or more groups selected from straight chain or branched chain alkyl, cycloalkyl, heterocycloalkyl, aryl, aralkyl, heteroaryl, heteroaralkyl or a heterosubstituent, and optionally including any of O, S, N in the straight chain, branched chain or cyclic structure; or R$^2$ and R$^4$ form a bond; wherein at least one of R$^1$, R$^2$, R$^3$ and R$^4$ is not hydrogen;

R$^5$, R$^6$, R$^7$ and R$^8$ can be the same or different and each independently represents H, straight chain or branched chain alkyl, cycloalkyl, heterocycloalkyl, aryl, aralkyl, heteroaryl, heteroaralkyl, each being optionally substituted by one or more groups selected from straight chain or branched chain alkyl, cycloalkyl, heterocycloalkyl, alkenyl, alkynyl, aryl, aralkyl, heteroaryl, heteroaralkyl, or a heterosubstituent, or a heterosubstituent; or at least two of R$^5$, R$^6$, R$^7$ and R$^8$ may each form a cyclic 3 to 20 membered hydrocarbon ring structure which may further be substituted by one or more groups selected from straight chain or branched chain alkyl, cycloalkyl, heterocycloalkyl, aryl, aralkyl, heteroaryl, heteroaralkyl or a heterosubstituent, and optionally including any of O, S, N in the straight chain, branched chain or cyclic structure; wherein preferably at least one of R$^5$, R$^6$, R$^7$ and R$^8$ is not hydrogen;

the metal of the coordinated transition metal catalyst is selected from a metal of the Iron-group, Cobalt-group, Nickel-group or Copper group;

the ligand of the coordinated transition metal catalyst is selected from compounds having the ability to coordinate to said transition metal, including phosphorous-, nitrogen-, As-, Sb- or N-heterocyclic based ligands; and the Lewis acid co-catalyst is selected from compounds of aluminum, boron, zinc, titanium, scandium.

By choosing the substituents R$^1$ to R$^8$ and thus defining the starting compounds of the process, the reaction can be controlled in such way that the reaction equilibrium can be shifted from one side to the other. This can be preferably done by reacting the starting compounds to yield a reaction mixture from which one of the formed products is removed from the reaction system, for example by evaporation of a side-product (eg gas). Alternatively, the introduction of strain (eg ring strain) or steric constraints in one of the reactants can also be used to drive the reaction.

Preferably, R$^1$, R$^2$, R$^3$ and R$^4$ can be the same or different and each independently represents aryl, heteroaryl, aralkyl, or heteroaralkyl, each being optionally substituted by one or more groups selected from straight chain or branched chain alkyl, cycloalkyl, heterocycloalkyl, alkenyl, alkynyl, aryl, aralkyl, heteroaryl, heteroaralkyl or a heterosubstituent, or a heterosubstituent, or R$^2$ and R$^4$ form a bond; wherein at least one of R$^1$, R$^2$, R$^3$ and R$^4$ is not hydrogen.

In some embodiments, R$^5$, R$^6$, R$^7$ and R$^8$ can be the same or different and each independently represents H, straight chain or branched chain alkyl, cycloalkyl, heterocycloalkyl, each being optionally substituted by one or more groups selected from straight chain or branched chain alkyl, cycloalkyl, heterocycloalkyl, alkenyl, alkynyl, aryl, aralkyl, heteroaryl, heteroaralkyl or a heterosubstituent, or a heterosubstituent, or at least two of R$^5$, R$^6$, R$^7$ and R$^8$ may each form a cyclic 3 to 20 membered hydrocarbon ring structure which may further be substituted by one or more groups selected from alkyl, cycloalkyl, heterocycloalkyl, aryl, heteroaryl or heterosubstituent, and optionally including any of O, S, N in the straight chain, branched chain or cyclic structure, wherein preferably at least one of R$^5$, R$^6$, R$^7$ and R$^8$ is not hydrogen.

In further embodiments, R$^5$, R$^6$, R$^7$ and R$^8$ can be the same or different and each independently represents H, straight chain or branched chain alkyl, or cycloalkyl, or at least two of R$^5$, R$^6$, R$^7$ and R$^8$ may each form a cyclic 3 to 20 membered aliphatic hydrocarbon ring structure which may further be substituted by one or more groups selected from alkyl, cycloalkyl, heterocycloalkyl, or heterosubstituent, and optionally including any of O, S, N in the straight chain, branched chain or cyclic structure, wherein at least one of R$^5$, R$^6$, R$^7$ and R$^8$ is not hydrogen.

In some embodiments, the compound of formula (II) is a lower alkyl nitrile having 1 to 6 carbon atoms, optionally substituted by one or more heterosubstituents.

In some embodiments, the compound of formula (I) is preferably a cyclic unsaturated hydrocarbon having 4 to 20, preferably 4 to 12 carbon atoms optionally substituted by one or more heterosubstituents. Unsaturated includes at least one of a double or triple bond.

The inventors have evaluated a range of metals for use as coordinated metalcatalysts to develop the transfer hydrocyanation reaction. Amongst the transition metal catalysts, transition metals and compounds thereof, selected from the Iron-group, Cobalt-group, Nickel-group or Copper group, the groups 8 to 11 of the periodic table, particularly Nickel, Cobalt and Palladium, are preferred. Examples are Ni(COD)$_2$, Ni(acac)$_2$, Ni(CO)$_4$, Pd(dba)$_2$, Pd(OAc)$_2$, Co$_2$(CO)$_8$ and preferred examples are Ni(COD)$_2$.

Nickel was initially chosen as a metal because Nickel(0) complexes have been shown to be the active species in the oxidative addition of inert bonds, including aliphatic C—CN bonds. However, initial experiments using simple Nickel catalysts alone failed to afford any product formation. Since Lewis Acids can both accelerate some Nickel-mediated reactions, the inventors made use of the addition of a Lewis Acid co-catalyst for facilitating the desired reversible transfer hydrocyanation mechanism.

The inventors also evaluated a range of ligands to increase the activity of the coordinated metal catalyst in the transfer hydrocyanation reaction. The ligand can be selected from compounds having the ability to coordinate to a transition metal, including phosphorous-, nitrogen-, As-, Sb- or N-heterocyclic based ligands. Examples are from the group consisting of phosphine ligands, particularly PPh$_3$, PCy$_3$, P(OPh)$_3$, PEt$_3$, BINAP, Xanthphos, DuPhos, DPEPhos, dppf, dppe, further preferred PPh$_3$ and DPEPhos, and mixtures thereof. Preferred examples are phosphine ligands, examples of which are DPEPhos, PPh$_3$, or mixtures thereof with the following meanings:

BINAP: 2,2'-Bis(diphenylphosphino)-1,1'-binaphthalene

Xanthphos: 4,5-Bis(diphenylphosphino)-9,9-dimethylxanthene

DPEPhos: (Oxydi-2,1-phenylene)bis(diphenylphosphine)

dppf: 1,1'-Ferrocenediyl-bis(diphenylphosphine)

dppe: 1,2-Bis(diphenylphosphino)ethane

The coordinated transition metal catalyst can be prepared in situ by addition of said ligands to a solution of the transition metal compound, said metal being selected from the Iron-group, Cobalt-group, Nickel-group or Copper group, the groups 8 to 11 of the periodic table, whereby coordinated transition metal catalysts with the metal Nickel, Cobalt or Palladium are preferred. Examples of such compounds to be added are $Ni(COD)_2$, $Ni(acac)_2$, $Ni(CO)_4$, $Pd(dba)_2$, $Pd(OAc)_2$, $Co_2(CO)_8$ and preferred example is $Ni(COD)_2$.

The Lewis acid co-catalyst can be any known Lewis acid catalyst having sufficient Lewis acid strength and can be selected from compounds of aluminum, boron, zinc, titanium, scandium. Examples are $Al(alkyl)_{3-Z}X_ZZ$, wherein alkyl is $C_1$ to $C_6$, Z is 0 to 3 and X is halogen, preferred chlorine, such as $AlMe_3$, $AlMe_2Cl$, $AlMeCl_2$, $AlCl_3$, $BPh_3$, $B(C_6F_5)_3$, $Zn(OTf)_2$, $ZnCl_2$, $TiCl_4$, $Sc(OTf)_3$, and preferred examples are $AlMe_3$, $AlMe_2Cl$, $AlCl_3$, $BPh_3$.

The solvent is not critical and can be selected amongst those which are commonly used for such kind of catalysed reactions, such as aromatic solvents such as toluene, benzene, xylene, cumene, chlorobenzene, dichlorobenzene, or aliphatic hydrocarbon solvents, depending on the specific reaction system.

The reaction temperature is usually in the range from 25 to 150° C., preferably from 25 to 125° C.

Definition for the substituents as used in the present formulae are given in the following.

A heterosubstituent according to the invention is to be understood as a substituent including heteroatoms, preferentially selected from O, N, S, Si and halogens. It can be preferentially selected from, =O, —OH, —F, —Cl, —Br, —I, —CN, —$N_3$, —$NO_2$, —$SO_3H$, NCO, NCS, OP(O)($OR^{S1}$)($OR^{S2}$), OP($OR^{S1}$)($OR^{S2}$), a monohalogenomethyl group, a dihalogenomethyl group, a trihalogenomethyl group, —$CF(CF_3)_2$, —$SF_5$, —$NR^{S1}_2$, —$OR^{S1}$, —$OOR^{S1}$, —$OSiR^{S1}R^{S2}R^{S3}$, —$OSi(OR^{S1})R^{S2}R^{S3}$, —$OSi(OR^{S1})(OR^{S2})R^{S3}$, —$OSi(OR^{S1})(OR^{S2})(OR^{S3})$, —$OSO_2R^{S1}$, —$S(O)R^{S1}$, —$S(O)_2R^{S1}$, —$C(O)OR^{S1}$, —$C(O)NR^{S1}R^{S2}$, —$NR^{S1}C(O)R^{S2}$, —C(O)—$R^{S1}$, —COOM, wherein M may be a metal such as Na, K or Cs.

$R^{S1}$ $R^{S2}$ and $R^{S3}$ each individually represent H, alkyl, cycloalkyl, heterocycloalkyl, aryl, heteroaryl, aralkyl, heteroaralkyl, sulfonyl, silyl, each being optionally substituted by one or more alkyl, cycloalkyl, heterocycloalkyl, heteroaryl, aralkyl, heteroaralkyl, sulfonyl or heterosubstituent.

For the reaction system in more detail, alkyl may be $C_1$-$C_{20}$-Alkyl which can be straight chain or branched or cyclic and has 1, 2, 3, 4, 5, 6, 7, 8, 9, 10, 11, 12, 13, 14, 15, 16, 17, 18, 19 or 20 carbon atoms. Alkyl might particularly be $C_1$-$C_6$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

Cycloalkyl may be a cyclic alkyl group forming a 3 to 20 membered ring and might be cyclopropyl, cyclobutyl, cyclopentyl, cyclohexyl, cycloheptyl or cyclooctyl.

Heterocycloalkyl may be a cycloalkyl forming a 3 to 10 membered ring and incorporating one or more heteroatoms selected from N, O and S within the cycle. In particular, heterocycloalkyls can be preferentially selected from 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Halogen is F, Cl, Br or I.

Aryl might be phenyl, naphthyl or biphenyl and substituted derivatives thereof.

Aralkyl might be benzyl, naphthylmethyl and substituted derivatives thereof.

Heteroaryl may have one or more heteroatoms selected from N, O, S and Si and is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benz-imidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

Heteroaralkyl might be any of the aforementioned heteroaryl bound to an alkyl group, such as pyridinylmethyl.

Optionally substituted means unsubstituted or monosubstituted, disubstituted, trisubstituted, tetrasubstituted, pentasubstituted, or even further substituted on the respective group.

Thus, the inventors have shown that a reaction pair of a coordinated transition metal catalyst and a Lewis acid co-catalyst can be used for a nitrile transfer reaction from an hydrocarbon nitrile to an unsaturated hydrocarbon, wherein
 the metal of the coordinated transition metal catalyst is selected from a metal of the Iron-group, Cobalt-group, Nickel-group or Copper group;
 the ligand of the coordinated transition metal catalyst is selected from compounds having the ability to coordinate to said transition metal, including phosphorous-, nitrogen-, As-, Sb- or N-heterocyclic based ligands; and
 the Lewis acid co-catalyst is selected from compounds of aluminum, boron, zinc, titanium, scandium,
 so that nitrile compounds are accessible without the need of using hydrogen cyanide.

The invention is further illustrated in the attached drawings and the following experimental section below.

In the attached drawings.

EXPERIMENTAL SECTION

Figure 2:
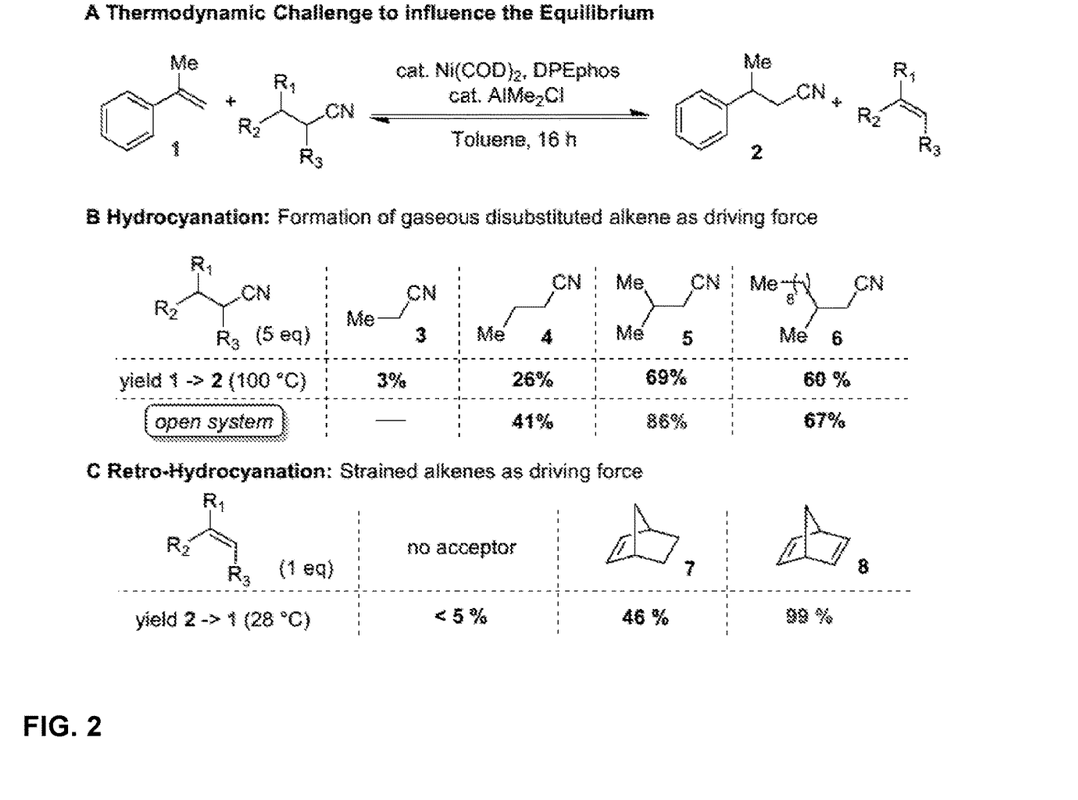
FIG. 2 shows the:
(A) Model reaction.
(B) Reagent optimization for hydrocyanation 1→2.
(C) Reagent optimization for retro-hydrocyanation 2→1.

After successfully finding initial reactivity using a Nickel catalyst and an Al co-catalyst, the inventors developed the ideas for efficiently manipulating the reaction equilibrium and they have found suitable alkene and alkyl nitrile reagents that allow to selectively drive the forward reaction from 1→2 and the reverse reaction from 2→1 under appropriate conditions (FIG. 2). Considering other metal catalyzed reversible reactions, such as the alkene metathesis reaction, the inventors reasoned that the use of simple driving forces, such as the extrusion of a gaseous side product or the release of ring strain, would efficiently shift the thermodynamic equilibrium to afford the desired product.

In the case of the forward reaction (FIG. 2B), hydrocyanation, the inventors evaluated a range of simple aliphatic nitriles (3-6) as potential hydrocyanating reagents and they found that (1) the degree of substitution of the alkene by-product correlates with the efficiency of the reaction in the order isobutylene>propene>ethylene, and (2) the formation of gaseous alkenes further improves the system, particularly when conducted in an open system. Thus, isovaleronitrile (5), which releases isobutylene as a gaseous byproduct, was identified as the best reagent for the hydrocyanation reaction of 1 and gave 86% yield of product 2 in toluene at 100° C. in the presence of catalytic Ni and Al.

Alternatively, alkyl nitrile product 2, formed in the forward reaction, can be used as test substrate to evaluate the efficiency of diverse alkene traps to drive the retro-hydrocyanation reaction to completion (FIG. 2C). A control reaction using no acceptor alkene did not lead to any significant formation of product 1. This result clearly shows that the formation of HCN and an alkene from an alkyl nitrile is thermodynamically disfavored, emphasizing the need to use an acceptor alkene to drive the process. Both norbornene (NBE, 7) and norbornadiene (NBD, 8) were then evaluated since they possess significant ring strain that should help to drive the retro-hydrocyanation reaction. Gratifyingly, NBD proved extremely efficient as a trapping reagent due to its high ring strain, affording good yields of the desired alkene product 1 at room temperature (RT).

Figure 3:
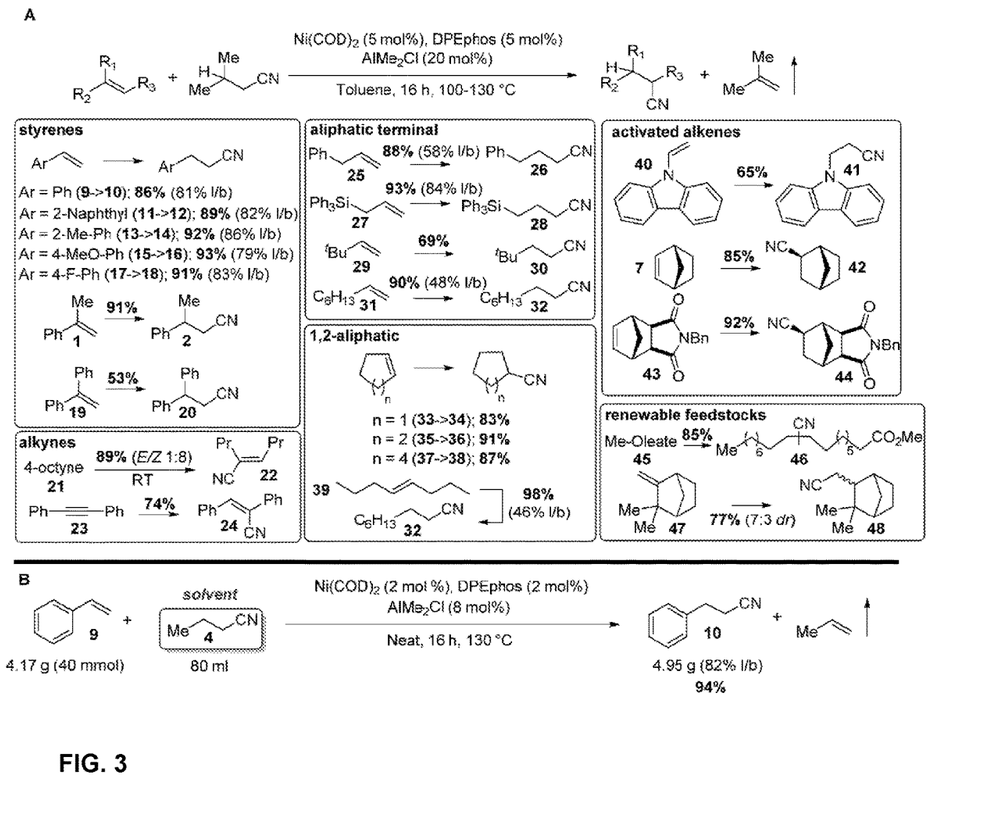
FIG. 3 shows the:
A. Scope of the hydrocyanation.
B. Scale-up experiment

Having demonstrated the ability of the inventors' reaction to be tuned on demand towards either side of the reaction, the inventors studied the scope of the hydrocyanation process (FIG. 3A). The transfer hydrocyanation of styrene derivatives gave the products in high yields and good linear to branched ratios (up to 85% for mono-substituted and full linear selectivity in the case of disubstituted styrenes 1 and 19), a selectivity complementary to previous protocols giving mostly the branched isomer. Non-activated, terminal aliphatic alkenes were also very active substrates in the transformation and gave the linear product as the major product (up to 100% l/b selectivity in the case of sterically congested tBu (30)). Next, the inventors investigated 1,2-disubstituted substrates. Cycloalkenes (33, 35 and 37) and strained norbornenes (7 and 43) were well tolerated and afforded the cyanated products in high yields. Two renewable feedstocks, methyl oleate (45) and camphene (47), were subjected to the reaction conditions and high yields of the products were obtained. Remarkably, the inventors' catalytic reaction could also be extended to the efficient hydrocyanation of both conjugated (23) and aliphatic alkynes (21) in good yields. Finally, the reaction of styrene (9) could be performed on a preparative scale (5 g) using inexpensive butyronitrile (4) as a reagent and solvent and 2 mol % of Ni catalyst to give the product in 94% yield after distillation (FIG. 3B).

The invention is further illustrated by the following non limiting examples.

Examples

Preparation Examples

General Procedure for the Preparation of Nitriles

A: General Procedure for the Preparation of Alkyl Nitriles

To a 0° C. solution of corresponding alkyl alcohol (5 mmol) in $CH_2Cl_2$ (5 mL) were added pyridine (2 mL), and 4-toluenesulfonyl chloride (1.06 g, 5.56 mmol). The resultant reaction mixture was stirred at room temperature for overnight. After that time, water was added and the resultant mixture extracted with $CH_2Cl_2$. The combined organic layers were subsequently washed with a 2M aqueous solution of HCl, a saturated aqueous solution of $NaHCO_3$, and brine and dried over anhydrous $Na_2SO_4$. After the desiccant was removed, the solvent was distilled off under vacuum to give the corresponding alkyl p-toluenesulfonate in quantitative yield and was used without any further purification.

To a solution of alkyl p-toluenesulfonate (ca. 5 mmol) in DMSO (10 mL) was added powdered NaCN (0.49 g, 10 mmol), and the mixture was stirred at 100° C. for 5 hours. After completion of the reaction, the reaction was cooled down to room temperature and quenched with saturated aqueous solution of $Na_2CO_3$. The aqueous phase was extracted with methyl tert-butyl ether (3*20 mL), the combined organic layers were washed several times with brine and dried over anhydrous $Na_2SO_4$. The solution was concentrated in vacuo, and purified by flash column chromatography on silica gel (pentane/methyl tert-butyl ether=10/1) to give the corresponding alkyl nitrile in high yield.

B: General Procedure for the Preparation of α-alkyl Benzyl Nitriles

Lithium bis(trimethylsilyl)amide (5.5 mL, 5.50 mmol; 1M solution in tetrahydrofuran) was added dropwise to a stirred solution of 2-phenylacetonitrile derivative (5.0 mmol) in anhydrous tetrahydrofuran (20 mL) at −78° C. under an atmosphere of argon. The anion was allowed to form over ca. 30 minutes, then corresponding bromide (5.25 mmol) was added dropwise and the reaction allowed to stir for ca. 1 hour before being slowly warmed to room temperature and stirred until completion (t.l.c. control). The reaction mixture was then quenched by addition of saturated aqueous ammonium chloride solution and extracted with methyl tert-butyl ether. The organic layers were combined, dried (anhyd. $Na_2SO_4$), filtered and concentrated in vacuo to afford the crude product. Purification by flash column chromatography (silica gel, eluting with hexane/ethyl acetate) afforded the corresponding α-alkyl benzyl nitrile.

Example 1

2

Isovaleronitrile 5 (0.26 mL, 2.50 mmol), α-methylstyrene 1 (65 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube with a reflux condenser was taken out of the glove box, and was then connected to a continuous flow of argon (positive pressure: 0.4 bar) and heated at 130° C. for 16 hours. After cooling to room temperature, the reaction mixture was concentrated under reduced pressure and the residue purified by flash column chromatography on silica gel (pentane/methyl tert-butyl ether=10/1) to give 2 (66.1 mg, yield: 91%). $^1$H NMR (500 MHz, CDCl$_3$) δ 7.34-7.30 (m, 2H), 7.26-7.21 (m, 3H), 3.13 (h, J=7.0 Hz, 1H), 2.59 (dd, J=16.7, 6.5 Hz, 1H), 2.53 (dd, J=16.7, 7.6 Hz, 1H), 1.43 (d, J=7.0 Hz, 3H); $^{13}$C NMR (125 MHz, CDCl$_3$) δ 143.26, 128.99, 127.46, 126.67, 118.72, 36.65, 26.49, 20.80. The spectral data are consistent with those reported in the literature.

Example 2

20

Commercial sample

Isovaleronitrile 5 (0.26 mL, 2.50 mmol), 1,1-diphenylethylene 19 (88 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube with a reflux condenser was taken out of the glove box, and was then connected to a continuous flow of argon (positive pressure: 0.4 bar) and heated at 130° C. for 16 hours. After cooling to room temperature, the reaction mixture was concentrated under reduced pressure and the residue purified by flash column chromatography on silica gel (pentane/methyl tert-butyl ether=10/1) to give 20 (54.9 mg, yield: 53%). $^1$H NMR (500 MHz, CDCl$_3$) δ 7.39-7.36 (m, 4H), 7.32-7.26 (m, 6H), 4.42 (t, J=7.7 Hz, 1H), 3.07 (d, J=7.7 Hz, 2H); $^{13}$C NMR (125 MHz, CDCl$_3$) δ 141.34, 129.03, 127.66, 127.54, 118.55, 47.26, 24.36.

Example 3

34

Isovaleronitrile 5 (0.26 mL, 2.50 mmol), cyclopentene 33 (44 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 25 mL pressure tube under an argon atmosphere in a glove box. The pressure tube was taken out of the glove box and heated at 100° C. for 16 hours. After that time, the reaction was cooled down to room temperature, and n-dodecane (100 μL) as internal standard was added to the solution. The reaction mixture was analyzed by GC and the yield of 34 determined by comparing their peak areas to that of the internal standard. (Retention time: 6.38 min, GC yield: 83%)

Example 4

36

Isovaleronitrile 5 (0.26 mL, 2.50 mmol), cyclohexene 35 (51 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 25 mL pressure tube under an argon atmosphere in a glove box. The pressure tube was taken out of the glove box and heated at 100° C. for 16 hours. After that time, the reaction was cooled down to room temperature, and n-dodecane (100 μL) as internal standard was added to the solution. The reaction mixture was analyzed by GC and the yield of 36 determined by comparing their peak areas to that of the internal standard. (Retention time: 7.62 min, GC yield: 91%)

Example 5

38

Isovaleronitrile 5 (0.26 mL, 2.50 mmol), cyclooctene 37 (65 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube with a reflux condenser was taken out of the glove box, and was then connected to a continuous flow of argon (positive pressure: 0.4 bar) and heated at 130° C. for 16 hours. After cooling to room temperature, the reaction mixture was concentrated under reduced pressure and the residue purified by flash column chromatography on silica gel (pentane/methyl tert-butyl ether=10/1) to give 38 (59.7 mg, yield: 87%). $^1$H NMR (500 MHz, CDCl$_3$): δ 2.78-2.73 (m, 1H), 1.98-1.92 (m, 2H), 1.87-1.72 (m, 4H), 1.60-1.47 (m, 8H); $^{13}$C NMR (125 MHz, CDCl$_3$) δ 123.69, 29.58, 28.87, 26.96, 25.26, 24.39. The spectral data are consistent with those reported in the literature.

Example 6

Isovaleronitrile 5 (0.26 mL, 2.50 mmol), norbornene 7 (47.1 mg, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 25 mL pressure tube under an argon atmosphere in a glove box. The pressure tube was taken out of the glove box and heated at 100° C. for 16 hours. After cooling to room temperature, the reaction mixture directly purified by flash column chromatography on silica gel (pentane/methyl tert-butyl ether=10/1) to give 42 (51.5 mg, yield: 85%). $^1$H NMR (500 MHz, CDCl$_3$) δ 2.59 (d, J=3.5 Hz, 1H), 2.39 (d, J=3.6 Hz, 1H), 2.35 (ddd, J=9.1, 4.8, 1.6 Hz, 1H), 1.85-1.76 (m, 1H), 1.73-1.66 (m, 1H), 1.64-1.50 (m, 3H), 1.41-1.34 (m, 1H), 1.27-1.14 (m, 2H); $^{13}$C NMR (125 MHz, CDCl$_3$) δ 123.71, 41.90, 37.30, 36.20, 36.13, 31.18, 28.63, 28.50. HRMS-ESI (m/z): [M+Na]$^+$ calcd for C$_8$H$_{11}$NNa, 144.078368; found, 144.078550.

Example 7

Isovaleronitrile 5 (0.26 mL, 2.50 mmol), 43 (126.7 mg, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 25 mL pressure tube under an argon atmosphere in a glove box. The pressure tube was taken out of the glove box and heated at 100° C. for 16 hours. After cooling to room temperature, the reaction mixture was concentrated under reduced pressure and the residue purified by flash column chromatography on silica gel (pentane/ethyl acetate=2/1) to give 44 (128.9 mg, yield: 92%). $^1$H NMR (500 MHz, CDCl$_3$) δ 7.30-7.17 (m, 5H), 4.53 (s, 2H), 2.93 (s, 1H), 2.76 (d, J=3.3 Hz, 1H), 2.55 (q, J=7.1 Hz, 2H), 2.44 (ddd, J=9.1, 4.8, 1.6 Hz, 1H), 1.96-1.84 (m, 1H), 1.82-1.73 (m, 1H), 1.57-1.42 (m, 1H), 1.05 (d, J=11.9 Hz, 1H), $^{13}$C NMR (125 MHz, CDCl$_3$) δ 176.97, 176.36, 135.57, 128.79, 128.76, 128.17, 121.57, 47.49, 47.26, 44.22, 42.68, 39.35, 34.70, 32.24, 29.84. HRMS-ESI (m/z): [M+Na]$^+$ calcd for C$_{17}$H$_{16}$N$_2$O$_2$Na, 303.110396; found, 303.110200.

Example 8

Commercial sample

Isovaleronitrile 5 (0.26 mL, 2.50 mmol), styrene 9 (57.5 µL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube was taken out of the glove box, and was then connected to a continuous flow of argon (positive pressure: 0.4 bar) and heated at heated at 100° C. for 16 hours. After cooling to room temperature, the reaction mixture was analyzed by GC and the regioselectivity of 10 determined by comparing their peak areas (l/b: 81/19). The reaction mixture was concentrated under reduced pressure and the residue purified by flash column chromatography on silica gel (pentane/methyl tert-butyl ether=10/1) to give 10 (linear product: 45.9 mg, yield: 70%; branched product: 10.5 mg, yield: 16%).

Linear product: $^1$H NMR (500 MHz, CDCl$_3$) δ 7.29-7.23 (m, 2H), 7.22-7.17 (m, 1H), 7.17-7.12 (m, 2H), 2.86 (t, J=7.4 Hz, 2H), 2.52 (t, J=7.4 Hz, 2H); $^{13}$C NMR (125 MHz, CDCl$_3$) δ 138.13, 128.93, 128.34, 127.29, 119.24, 31.60, 19.41. Branched product: $^1$H NMR (500 MHz, CDCl$_3$) δ 7.42-7.31 (m, 5H), 3.90 (q, J=7.3 Hz, 1H), 1.65 (d, J=7.4 Hz, 3H); $^{13}$C NMR (125 MHz, CDCl$_3$) δ 137.19, 129.30, 128.19, 126.85, 121.74, 31.41, 21.63.

Example 9

Isovaleronitrile 5 (0.26 mL, 2.50 mmol), 2-vinylnaphthalene 11 (77.1 mg, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube was taken out of the glove box, and was then connected to a continuous flow of argon (positive pressure: 0.4 bar) and heated at heated at 100° C. for 16 hours. After cooling to room temperature, the reaction mixture was analyzed by GC and the regioselectivity of 12 determined by comparing their peak areas (I/b: 82/18). The reaction mixture was concentrated under reduced pressure and the residue purified by flash column chromatography on silica gel (pentane/methyl tert-butyl ether=10/1) to give 12 (linear product: 66.1 mg, yield: 73%; branched product: 14.5 mg, yield: 16%).

Linear product: $^1$H NMR (500 MHz, CDCl$_3$) δ 7.88-7.78 (m, 3H), 7.69 (s, 1H), 7.54-7.43 (m, 2H), 7.35 (dd, J=8.3, 1.8 Hz, 1H), 3.12 (t, J=7.4 Hz, 2H), 2.70 (t, J=7.5 Hz, 2H); $^{13}$C NMR (125 MHz, CDCl$_3$) δ 135.56, 133.59, 132.59, 128.77, 127.80, 127.75, 127.00, 126.48, 126.43, 126.04, 119.26, 31.82, 19.38. The spectral data are consistent with those reported in the literature.

Branched product: $^1$H NMR (500 MHz, CDCl$_3$) δ 7.92-7.79 (m, 4H), 7.56-7.48 (m, 2H), 7.43 (dd, J=8.5, 1.9 Hz, 1H), 4.07 (q, J=7.4 Hz, 1H), 1.73 (d, J=7.3 Hz, 3H); $^{13}$C NMR (125 MHz, CDCl$_3$) δ 134.44, 133.44, 132.90, 129.27, 127.98, 127.85, 126.87, 126.62, 125.71, 124.54, 121.72, 31.55, 21.57. The spectral data are consistent with those reported in the literature.

Example 10

14

Isovaleronitrile 5 (0.26 mL, 2.50 mmol), 2-methylstyrene 13 (65 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube was taken out of the glove box, and was then connected to a continuous flow of argon (positive pressure: 0.4 bar) and heated at heated at 100° C. for 16 hours. After cooling to room temperature, the reaction mixture was analyzed by GC and the regioselectivity of 14 determined by comparing their peak areas (I/b: 86/14). The reaction mixture was concentrated under reduced pressure and the residue purified by flash column chromatography on silica gel (pentane/methyl tert-butyl ether=10/1) to give 14 (linear product: 57.3 mg, yield: 79%; branched product: 9.4 mg, yield: 13%).

Linear product: $^1$H NMR (500 MHz, CDCl$_3$) δ 7.23-7.14 (m, 4H), 2.98 (t, J=7.7 Hz, 2H), 2.59 (t, J=7.7 Hz, 2H), 2.34 (s, 3H); $^{13}$C NMR (125 MHz, CDCl$_3$) δ 136.34, 135.91, 130.78, 128.84, 127.50, 126.62, 119.35, 29.01, 19.30, 18.14. The spectral data are consistent with those reported in the literature.

Branched product: $^1$H NMR (500 MHz, CDCl$_3$) δ 7.45 (dd, J=7.3, 1.7 Hz, 1H), 7.29-7.17 (m, 3H), 4.05 (q, J=7.2 Hz, 1H), 2.37 (s, 3H), 1.61 (d, J=7.2 Hz, 3H); $^{13}$C NMR (125 MHz, CDCl$_3$) δ 135.38, 134.90, 131.12, 128.26, 127.13, 126.84, 121.94, 28.30, 20.18, 19.15. The spectral data are consistent with those reported in the literature.

Example 11

Isovaleronitrile 5 (0.26 mL, 2.50 mmol), 4-vinylanisole 15 (66.5 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube was taken out of the glove box, and was then connected to a continuous flow of argon (positive pressure: 0.4 bar) and heated at heated at 100° C. for 16 hours. After cooling to room temperature, the reaction mixture was analyzed by GC and the regioselectivity of 16 determined by comparing their peak areas (I/b: 79/21). The reaction mixture was concentrated under reduced pressure and the residue purified by flash column chromatography on silica gel (pentane/methyl tert-butyl ether=5/1) to give 16 (linear product: 59.6 mg, yield: 74%; branched product: 15.3 mg, yield: 19%).

Linear product: $^1$H NMR (500 MHz, CDCl$_3$) δ 7.18-7.12 (m, 2H), 6.90-6.83 (m, 2H), 3.80 (s, 3H), 2.90 (t, J=7.3 Hz, 2H), 2.58 (t, J=7.4 Hz, 2H); $^{13}$C NMR (125 MHz, CDCl$_3$) δ 158.85, 130.24, 129.44, 119.38, 114.35, 55.40, 30.87, 19.82. The spectral data are consistent with those reported in the literature.

Branched product: $^1$H NMR (500 MHz, CDCl$_3$) δ 7.32-7.21 (m, 2H), 6.95-6.85 (m, 2H), 3.85 (q, J=7.3 Hz, 1H), 3.81 (s, 3H), 1.62 (d, J=7.3 Hz, 3H); $^{13}$C NMR (125 MHz, CDCl$_3$) δ 159.43, 129.21, 127.98, 122.01, 114.60, 55.50, 30.61, 21.68.

The spectral data are consistent with those reported in the literature.

Example 12

Isovaleronitrile 5 (0.26 mL, 2.50 mmol), 4-fluorostyrene 17 (60 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube was taken out of the glove box, and was then connected to a continuous flow of argon (positive pressure:

0.4 bar) and heated at heated at 100° C. for 16 hours. After cooling to room temperature, the reaction mixture was analyzed by GC and the regioselectivity of 18 determined by comparing their peak areas (l/b: 83/17). The reaction mixture was concentrated under reduced pressure and the residue purified by flash column chromatography on silica gel (pentane/methyl tert-butyl ether=10/1) to give 18 (linear product: 56.7 mg, yield: 76%; branched product: 11.2 mg, yield: 15%).

Linear product: $^1$H NMR (500 MHz, CDCl$_3$) δ 7.23-7.17 (m, 2H), 7.06-6.98 (m, 2H), 2.93 (t, J=7.3 Hz, 2H), 2.60 (t, J=7.3 Hz, 2H); $^{13}$C NMR (126 MHz, CDCl$_3$) 162.11 (d, $J_{C-F}$=243.75 Hz), 133.81, 129.98 (d, $J_{C-F}$=7.50 Hz), 119.06, 115.84 (d, $J_{C-F}$=21.25 Hz), 30.86, 19.67. The spectral data are consistent with those reported in the literature.

Branched product: $^1$H NMR (500 MHz, CDCl$_3$) δ 7.36-7.29 (m, 2H), 7.10-7.04 (m, 2H), 3.89 (q, J=7.3 Hz, 1H), 1.63 (d, J=7.3 Hz, 3H); $^{13}$C NMR (125 MHz, CDCl$_3$) δ 162.47 (d, $J_{C-F}$=245.12 Hz), 132.97, 128.56 (d, $J_{C-F}$=8.25 Hz), 121.53, 116.23 (d, $J_{C-F}$=22.12 Hz), 30.71, 21.65. The spectral data are consistent with those reported in the literature.

Example 13

Isovaleronitrile 5 (0.26 mL, 2.50 mmol), allyltriphenylsilane 27 (150.2 mg, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube connected with a reflux condenser was taken out of the glove box, and was subsequently connected to a continuous flow of argon (positive pressure: 0.4 bar) and heated at 130° C. for 16 hours. After cooling to room temperature, the reaction mixture was analyzed by GC (Temperature program: 15° C./min to 180° C., 15° C./min to 300° C., 300° C. (15 min)) and the regioselectivity of 28 determined by comparing their peak areas (l/b: 84/16). The reaction mixture was concentrated under reduced pressure and the residue purified by flash column chromatography on silica gel (pentane/methyl tert-butyl ether=10/1) to give 28 (linear product: 127.7 mg, yield: 78%; branched product: 24.5 mg, yield: 15%).

Linear product: $^1$H NMR (500 MHz, CDCl$_3$) δ 7.54-7.49 (m, 6H), 7.46-7.35 (m, 9H), 2.37 (t, J=6.9 Hz, 2H), 1.88-1.78 (m, 2H), 1.57-1.49 (m, 2H); $^{13}$C NMR (125 MHz, CDCl$_3$) δ 135.66, 134.18, 129.90, 128.22, 119.75, 20.94, 20.82, 13.13. HRMS-EI (m/z): [M]$^+$ calcd for C$_{22}$H$_{21}$NSi, 327.144327; found, 327.144175.

Branched product: $^1$H NMR (500 MHz, CDCl$_3$) δ 7.60-7.53 (m, 6H), 7.49-7.37 (m, 9H), 2.73 (sext, J=7.0 Hz, 1H), 1.97 (dd, J=15.2, 7.0 Hz, 1H), 1.68 (dd, J=15.2, 7.8 Hz, 1H), 1.27 (d, J=7.0 Hz, 3H); $^{13}$C NMR (125 MHz, CDCl$_3$) δ 135.73, 133.45, 130.15, 128.31, 124.07, 21.67, 21.47, 19.19. HRMS-EI (m/z): [M]$^+$ calcd for C$_{22}$H$_{21}$NSi, 327.144327; found, 327.144029.

Example 14

Isovaleronitrile 5 (0.26 mL, 2.50 mmol), allylbenzene 25 (66 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube connected with a reflux condenser was taken out of the glove box, and was subsequently connected to a continuous flow of argon (positive pressure: 0.4 bar) and heated at 130° C. for 16 hours. After that time, the reaction was cooled down to room temperature, and n-dodecane (100 μL) as internal standard was added to the solution. The reaction mixture was analyzed by GC and the yield of 26 determined by comparing their peak areas to that of the internal standard. (GC yield: 88%, ratio of regioisomers: 58/29/13, retention time: 11.48, 10.77, 10.56 min respectively).

Example 15

Isovaleronitrile 5 (0.26 mL, 2.50 mmol), 3,3-dimethyl-1-butene 29 (65 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 25 mL pressure tube under an argon atmosphere in a glove box. The pressure tube was taken out of the glove box and heated at 100° C. for 16 hours. After cooling to room temperature, the reaction mixture directly purified by flash column chromatography on silica gel (pentane/methyl tert-butyl ether=10/1) to give 30 (38.4 mg, yield: 69%). $^1$H NMR (500 MHz, CDCl$_3$) δ 2.31-2.25 (m, 2H), 1.64-1.59 (m, 2H), 0.93 (s, 9H); $^{13}$C NMR (125 MHz, CDCl$_3$) δ 120.74, 39.33, 30.48, 28.80, 12.87. The spectral data are consistent with those reported in the literature.

Example 16

-continued

Isovaleronitrile 5 (0.26 mL, 2.50 mmol), 1-octene 31 (78.5 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube with a reflux condenser was taken out of the glove box, and was subsequently connected to a continuous flow of argon (positive pressure: 0.4 bar) and heated at 130° C. for 16 hours. After that time, the reaction was cooled down to room temperature, and n-dodecane (100 μL) as internal standard was added to the solution. The reaction mixture was analyzed by GC and the yield of desired product determined by comparing their peak areas to that of the internal standard. (GC yield: 90%, ratio of regioisomers: 48/32/11/9, retention time: 9.70, 8.95, 8.81, 8.71 min respectively).

Example 17

Isovaleronitrile 5 (0.26 mL, 2.50 mmol), trans-4-octene 39 (78.5 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube connected with a reflux condenser was taken out of the glove box, and was subsequently connected to a continuous flow of argon (positive pressure: 0.4 bar) and heated at 130° C. for 16 hours. After that time, the reaction was cooled down to room temperature, and n-dodecane (100 μL) as internal standard was added to the solution. The reaction mixture was analyzed by GC and the yield of desired product determined by comparing their peak areas to that of the internal standard. (GC yield: 98%, ratio of regioisomers: 46/30/12/12, retention time: 9.70, 8.95, 8.81, 8.71 min respectively).

Example 18

Isovaleronitrile 5 (0.26 mL, 2.50 mmol), N-vinylcarbazole 40 (96.6 mg, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube connected with a reflux condenser was taken out of the glove box, and was subsequently connected to a continuous flow of argon (positive pressure: 0.4 bar) and heated at 130° C. for 16 hours. After cooling to room temperature, the reaction mixture was concentrated under reduced pressure and the residue purified by flash column chromatography on silica gel (pentane/ethyl acetate=2/1) to give 41 (71.6 mg, yield: 65%). $^1$H NMR (500 MHz, CDCl$_3$) δ 8.11 (d, J=8.1 Hz, 2H), 7.54-7.48 (m, 2H), 7.41 (d, J=8.1 Hz, 2H), 7.33-7.27 (m, 2H), 4.65 (t, J=7.2 Hz, 2H), 2.84 (t, J=7.2 Hz, 2H); $^{13}$C NMR (125 MHz, CDCl$_3$) δ 139.62, 126.33, 123.48, 120.85, 120.09, 117.46, 108.26, 39.02, 17.39. HRMS-ESI (m/z): [M+Na]$^+$ calcd for C$_{15}$H$_{12}$N$_2$Na, 243.089266; found, 243.089470.

Example 19

Isovaleronitrile 5 (0.26 mL, 2.50 mmol), camphene 47 (68 mg, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube connected with a reflux condenser was taken out of the glove box, and was subsequently connected to a continuous flow of argon (positive pressure: 0.4 bar) and heated at 130° C. for 16 hours. After cooling to room temperature, the reaction mixture was concentrated under reduced pressure and the residue purified by flash column chromatography on silica gel (pentane/methyl tert-butyl ether=10/1) to give 48 (62.8 mg, yield: 77%, diastereoselectivity based on $^1$H NMR: 7/3). $^1$H NMR (500 MHz, CDCl$_3$) δ 2.35-2.18 (m, 3.42H), 2.15-2.09 (m, 0.84H), 1.84-1.79 (m, 2H), 1.76-1.74 (m, 0.42H), 1.69-1.64 (m, 1.42H), 1.63-1.61 (m, 0.42H), 1.59-1.54 (m, 1H), 1.44 (ddd, J=8.9, 6.7, 1.7 Hz, 0.42H),

1.37-1.30 (m, 2H), 1.25-1.23 (m, 3.26H), 1.16 (dt, J=10.2, 1.6 Hz, 0.42H), 1.04 (s, 1.28H), 1.02 (s, 3H), 0.94 (s, 1.28H), 0.87 (s, 3H); $^{13}$C NMR (125 MHz, CDCl$_3$) δ 120.36, 50.74, 49.54, 49.02, 47.36, 43.84, 42.13, 37.11, 36.92, 35.61, 32.04, 29.86, 29.49, 27.71, 24.56, 24.47, 23.94, 21.07, 20.11, 19.04, 15.36. HRMS-ESI (m/z): [M+Na]$^+$ calcd for C$_{11}$H$_{17}$NNa, 186.125318; found, 186.125480.

Example 20

Isovaleronitrile 5 (0.26 mL, 2.50 mmol), 99% purity of methyl oleate 45 (170 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 10 mL Schlenk tube under an argon atmosphere in a glove box. The Schlenk tube connected with a reflux condenser was taken out of the glove box, and was subsequently connected to a continuous flow of argon (positive pressure: 0.4 bar) and heated at 130° C. for 16 hours. After cooling to room temperature, the reaction mixture was concentrated under reduced pressure and the residue purified by flash column chromatography on silica gel (pentane/methyl tert-butyl ether=5/1) to give 46 (137.5 mg, yield: 85%). $^1$H NMR (500 MHz, CDCl$_3$) δ 3.77-3.60 (m, 3H), 2.57-2.41 (m, 1H), 2.36-2.24 (m, 2H), 1.65-1.50 (m, 7H), 1.46-1.37 (m, 2H), 1.31-1.24 (m, 19H), 0.98-0.84 (m, 3H); $^{13}$C NMR (125 MHz, CDCl$_3$) δ 174.49 (—CO$_2$), 122.63 (—CN). HRMS-ESI (m/z): [M+Na]$^+$ calcd for C$_{20}$H$_{37}$NO$_2$Na, 346.271648; found, 346.271560. It should be noted that the isolated product 46 containing 9 regioisomers which were observed by GC analysis (Temperature program: 15° C./min to 180° C.; 15° C./min to 300° C.; 300° C. (15 min)).

Example 21

Isovaleronitrile 5 (0.26 mL, 2.50 mmol), 4-octyne 21 (73 μL, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 4 mL Screw-cap vial under an argon atmosphere in a glove box. The vial was taken out of the glove box, the temperature of which was fixed at 28° C. The reaction mixture was stirred for 16 hours at 28° C. After that time, the reaction mixture directly purified by flash column chromatography on silica gel (pentane/methyl tert-butyl ether=10/1) to give 22 (51.5 mg, yield: 89%, the ratio of Z/E based on $^1$H NMR: 8/1).

Z-product: $^1$H NMR (500 MHz, CDCl$_3$) δ 6.35 (tt, J=7.6, 1.2 Hz, 1H), 2.20-2.13 (m, 4H), 1.57 (sext, J=7.4 Hz, 2H), 1.45 (sext, J=7.4 Hz, 2H), 0.96-0.91 (m, 6H); $^{13}$C NMR (125 MHz, CDCl$_3$) δ 148.32, 120.37, 115.03, 30.54, 30.51, 21.92, 21.43, 13.85, 13.50. The spectral data are consistent with those reported in the literature.

HRMS-ESI (m/z): [M+Na]$^+$ calcd for C$_9$H$_{15}$NNa, 160.109668; found, 160.109800.

Example 22

Isovaleronitrile 5 (0.26 mL, 2.50 mmol), diphenylacetylene 23 (89 mg, 0.50 mmol) and 1.0M solution of AlMe$_2$Cl in hexane (0.10 mL, 0.10 mmol) were added sequentially to a solution of Ni(COD)$_2$ (6.9 mg, 5 mol %) and DPEphos (13.5 mg, 5 mol %) in toluene (1.0 mL) prepared in a 25 mL pressure tube under an argon atmosphere in a glove box. The pressure tube was taken out of the glove box and heated at 100° C. for 16 hours. After cooling to room temperature, the reaction mixture was concentrated under reduced pressure and the residue purified by flash column chromatography on silica gel (pentane/methyl tert-butyl ether=10/1) to give 24 (75.9 mg, yield: 74%). $^1$H NMR (500 MHz, CDCl$_3$) δ 7.92-7.88 (m, 2H), 7.71-7.67 (m, 2H), 7.55 (s, 1H), 7.51-7.39 (m, 6H); $^{13}$C NMR (125 MHz, CDCl$_3$) δ 142.39, 134.58, 133.83, 130.67, 129.39, 129.33, 129.19, 129.09, 126.12, 118.13, 111.80. The spectral data are consistent with those reported in the literature.

Example 23

Example 23 refers to a Scale-up experiment as illustrated in FIG. 3B. Styrene 9 (4.58 mL, 40 mmol) and 1.0M solution of AlMe$_2$Cl in hexane (3.2 mL, 3.2 mmol, 8 mol %) were added sequentially to a solution of Ni(COD)$_2$ (220.0 mg, 2 mol %) and DPEphos (430.8 mg, 2 mol %) in butyronitrile 4 (80 mL) prepared in a 250 mL round bottle flask under an argon atmosphere in a glove box. The flask with a reflux condenser was taken out of the glove box, and was then connected to a continuous flow of argon (positive pressure: 0.4 bar) and heated at 130° C. for 16 hours. After cooling to room temperature, the reaction was quenched with methanol and the mixture was filtered through celite to remove the solid. The reaction mixture was analyzed by GC and the regioselectivity of 10 determined by comparing their peak areas (l/b: 82/18). The methanol and butyronitrile were distilled off under vacuum. The residue was directly purified by bulb-to-bulb distillation (Buchi Glass oven B-585) to give the desired product in 94% yield (4.95 g).

Example 24

69 (82.6 mg, 0.50 mmol), norbornadiene 8 (51 µL, 0.5 mmol) and 1.0M solution of AlMe$_2$Cl in hexane (50 µL, 10.0 mol %, 0.05 mmol) were added sequentially to a solution of Ni(COD)$_2$ (3.45 mg, 2.5 mol %, 12.5 µmol) and DPEphos (6.75 mg, 2.5 mol %, 12.5 µmol) in benzene (1.0 mL) prepared in a 4 mL Screw-cap vial under an argon atmosphere in a glove box. The vial was taken out of the glove box, the temperature of which was fixed at 28° C. The reaction mixture was stirred for 16 hours at 28° C. After that time, the reaction mixture was concentrated under reduced pressure and the residue purified by flash column chromatography on silica gel (100% pentane) to 70 (49.0 mg, yield: 71%). $^1$H NMR (500 MHz, CDCl$_3$) 5.74-5.64 (m, 1H), 5.13-5.06 (m, 1H), 4.99-4.88 (m, 2H), 2.12 (p, J=7.0 Hz, 1H), 2.01-1.89 (m, 2H), 1.68 (s, 3H), 1.60 (s, 3H), 1.35-1.26 (m, 2H), 0.99 (d, J=6.9 Hz, 3H); $^{13}$C NMR (125 MHz, CDCl$_3$) δ 144.91, 131.44, 124.80, 112.61, 37.51, 36.89, 25.88, 20.30, 17.83.

Further experimental work of the inventors evidenced that other reaction systems with different ligands, Lewis acids and/or different metals also lead to satisfying conversion results as illustrated in the following Schemes.

Scheme 1-Different LIgands

Scheme 2-Different Metals

L =

Schemes 3-Different ligands and Lewis acids

Ni(COD)₂/Ligand
Lewis acid
Toluene
100° C., 16 h

L1

L2

L3

L4

L5

L6

L7

L9

L9

L10

| Entry | Catalyst | Ligand | Lewis acid | Conversion | Yield |
|---|---|---|---|---|---|
| 1 | Ni(COD)₂ | PPh₃ | AlMe₂Cl | 73% | 58% |
| 2 | Ni(COD)₂ | L1 | AlMe₂Cl | 71% | 59% |
| 3 | Ni(COD)₂ | L2 | AlMe₂Cl | 69% | 46% |
| 4 | Ni(COD)₂ | P(Et)₃ | AlMe₂Cl | 41% | 25% |
| 5 | Ni(COD)₂ | L3 | AlMe₂Cl | 67% | 56% |
| 6 | Ni(COD)₂ | L4 | AlMe₂Cl | 75% | 69% |
| 7 | Ni(COD)₂ | L4 | AlCl₃ | 49% | 41% |
| 8 | Ni(COD)₂ | L4 | AlMe3 | 70% | 65% |
| 9 | Ni(COD)₂ | L5 | AlMe₂Cl | 65% | 49% |
| 10 | Ni(COD)₂ | L6 | AlMe₂Cl | 76% | 55% |
| 11 | Ni(COD)₂ | L7 | AlMe₂Cl | 65% | 41% |
| 12 | Ni(COD)₂ | L8 | AlMe₂Cl | 80% | 52% |
| 13 | Ni(COD)₂ | L9 | AlMe₂Cl | 37% | 30% |
| 14 | Ni(COD)₂ | L10 | AlMe₂Cl | 36% | 29% |

The inventors have shown in the above experimental results that a metal-catalyzed, in particular, Ni-catalyzed transfer hydrocyanation reaction between alkyl nitriles and alkenes can be fully manipulated to produce either product selectively using simple driving forces. This exceptionally powerful synthetic tool could be applied to the catalytic hydrocyanation and retro-hydrocyanation of a wide range of structurally different molecules (>40 examples) without relying on the use of highly toxic HCN. In a broader context, the functional group metathesis strategy delineated in this invention will likely be a milestone in the development of reversible hydrofunctionalization reactions of alkenes that do not rely on the use of hazardous gases.

The invention claimed is:

1. A process for effecting a catalytic reversible alkene-nitrile interconversion, said process comprising reacting an unsaturated hydrocarbon (I) with an alkylnitrile (II) in the presence of a transition metal coordinated to a ligand and a Lewis acid co-catalyst, optionally in a solvent, to yield an alkylnitrile (III) and an unsaturated hydrocarbon (IV), alkylnitrile (III) and unsaturated hydrocarbon (IV) being different from alkylnitrile (II) and unsaturated hydrocarbon (I), respectively, as represented in the following reaction scheme:

wherein:
  $R^1$, $R^2$, $R^3$ and $R^4$ can be the same or different and each independently represents H, straight chain or branched chain alkyl, cycloalkyl, heterocycloalkyl, aryl, aralkyl, heteroaryl, heteroaralkyl, each being optionally substituted by one or more groups selected from straight chain or branched chain alkyl, cycloalkyl, heterocycloalkyl, alkenyl, alkynyl, aryl, aralkyl, heteroaryl, heteroaralkyl or a heterosubstituent; or a heterosubstituent, or at least two of $R^1$, $R^2$, $R^3$ and $R^4$ may each form a cyclic 3 to 20 membered ring structure which may further be substituted by one or more groups selected from straight chain or branched chain alkyl, cycloalkyl, heterocycloalkyl, aryl, aralkyl, heteroaryl, heteroaralkyl or a heterosubstituent, and optionally including any of O, S, N in the straight chain, branched chain or cyclic structure; or $R^2$ and $R^4$ form a bond; wherein at least one of $R^1$, $R^2$, $R^3$ and $R^4$ is not hydrogen;
  $R^5$, $R^6$, $R^7$ and $R^8$ can be the same or different and each independently represents H, straight chain or branched chain alkyl, cycloalkyl, heterocycloalkyl, aryl, aralkyl, heteroaryl, heteroaralkyl, each being optionally substituted by one or more groups selected from straight chain or branched chain alkyl, cycloalkyl, heterocycloalkyl, alkenyl, alkynyl, aryl, aralkyl, heteroaryl, heteroaralkyl, or a heterosubstituent, or a heterosubstituent; or at least two of $R^5$, $R^6$, $R^7$ and $R^8$ may each form a cyclic 3 to 20 membered hydrocarbon ring structure which may further be substituted by one or more groups selected from straight chain or branched chain alkyl, cycloalkyl, heterocycloalkyl, aryl, aralkyl, heteroaryl, heteroaralkyl or a heterosubstituent, and optionally including any of O, S, N in the straight chain, branched chain or cyclic structure; wherein optionally at least one of $R^5$, $R^6$, $R^7$ and $R^8$ is not hydrogen;
  the metal of the coordinated transition metal catalyst is selected from a metal of the Iron-group, Cobalt-group, Nickel-group or Copper group;
  the ligand of the coordinated transition metal catalyst is selected from compounds having the ability to coordinate to said transition metal, optionally phosphorous-, nitrogen-, As-, Sb- or N-heterocyclic based ligands; and
  the Lewis acid co-catalyst is selected from compounds of aluminum, boron, zinc, titanium, scandium.

2. Process according to claim 1, wherein $R^1$, $R^2$, $R^3$ and $R^4$ can be the same or different and each independently represents H, aryl, aralkyl, heteroaryl, heteroaralkyl, each being optionally substituted by one or more groups selected from straight chain or branched chain alkyl, cycloalkyl, heterocycloalkyl, alkenyl, alkynyl, aryl, aralkyl, heteroaryl, heteroaralkyl or a heterosubstituent, or a heterosubstituent, or $R^2$ and $R^4$ form a bond; wherein at least one of $R^1$, $R^2$, $R^3$ and $R^4$ is not hydrogen.

3. Process according to claim 1, wherein $R^5$, $R^6$, $R^7$ and $R^8$ can be the same or different and each independently represents H, straight chain or branched chain alkyl, cycloalkyl, heterocycloalkyl, each being optionally substituted by one or more groups selected from straight chain or branched chain alkyl, cycloalkyl, heterocycloalkyl, alkenyl, alkynyl, aryl, aralkyl, heteroaryl, heteroaralkyl or a heterosubstituent, or a heterosubstituent, or at least two of $R^5$, $R^6$, $R^7$ and $R^8$ may each form a cyclic 3 to 20 membered hydrocarbon ring structure which may further be substituted by one or more groups selected from alkyl, cycloalkyl, heterocycloalkyl, aryl, heteroaryl or heterosubstituent, and optionally having any of O, S, N in the straight chain, branched chain or cyclic structure, wherein optionally at least one of $R^5$, $R^6$, $R^7$ and $R^8$ is not hydrogen.

4. Process according to claim 3, wherein $R^5$, $R^6$, $R^7$ and $R^8$ can be the same or different and each independently represents H, straight chain or branched chain alkyl, or cycloalkyl, or at least two of $R^5$, $R^6$, $R^7$ and $R^8$ may each form a cyclic 3 to 20 membered aliphatic hydrocarbon ring structure which may further be substituted by one or more groups selected from alkyl, cycloalkyl, heterocycloalkyl, or heterosubstituent, and optionally having any of O, S, N in the straight chain, branched chain or cyclic structure, wherein at least one of $R^5$, $R^6$, $R^7$ and $R^8$ is not hydrogen.

5. Process according to claim 3, wherein the compound of formula (II) is a lower alkyl nitrile having 1 to 6 carbon atoms, optionally substituted by one or more heterosubstituents.

6. Process according to claim 1, wherein the compound of formula (I) is a cyclic unsaturated hydrocarbon having 4 to 20 optionally substituted by one or more heterosubstituents.

7. Process according to claim 1, wherein the coordinated transition metal catalyst is obtained from a transition metal catalyst precursor selected from $Ni(COD)_2$, $Ni(acac)_2$, $Ni(CO)_4$, $Pd(dba)_2$, $Pd(OAc)_2$, $Co_2(CO)_8$.

8. Process according to claim 1, wherein the Lewis acid co-catalyst is selected from $AlMe_3$, $AlMe_2Cl$, $AlMeCl_2$, $AlCl_3$, $BPh_3$, $B(C_6F_5)_3$, $Zn(OTf)_2$, $ZnCl_2$, $TiCl_4$, and $Sc(OTf)_3$.

9. Process according to claim 1, wherein the ligand is selected from the group consisting of phosphine ligands, and mixtures thereof.

10. Method of using a reaction pair of a coordinated transition metal catalyst and a Lewis acid co-catalyst for a nitrile transfer reaction from an hydrocarbon nitrile to an unsaturated hydrocarbon, wherein
  the metal of the coordinated transition metal catalyst is selected from a metal of the Iron-group, Cobalt-group, Nickel-group or Copper group;
  the ligand of the coordinated transition metal catalyst is selected from compounds having the ability to coordinate to said transition metal, including phosphorous-, nitrogen-, As-, Sb- or N-heterocyclic based ligands; and the Lewis acid co-catalyst is selected from compounds of aluminum, boron, zinc, titanium, scandium.

11. Process according to claim 9, wherein the ligand is selected from the group consisting of $PPh_3$, $PCy_3$, $P(OPh)_3$, $PEt_3$, BINAP, Xanthphos, DuPhos, DPEPhos, dppf, dppe, and mixtures thereof.

* * * * *